(12) United States Patent
Haas et al.

(10) Patent No.: US 9,198,415 B2
(45) Date of Patent: Dec. 1, 2015

(54) PLANT IRRIGATION METHODS

(75) Inventors: Ulrich Johannes Haas, Stein (CH); Christophe Weider, Basel (CH); Ronald Zeun, Stein (CH); Albert Bassi, Greensboro, NC (US); Daniel Perkins, Yardley, PA (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 13/701,640

(22) PCT Filed: Jun. 3, 2011

(86) PCT No.: PCT/US2011/039082
§ 371 (c)(1),
(2), (4) Date: Jun. 4, 2013

(87) PCT Pub. No.: WO2011/153442
PCT Pub. Date: Dec. 8, 2011

(65) Prior Publication Data
US 2013/0247250 A1 Sep. 19, 2013

(30) Foreign Application Priority Data

Jun. 4, 2010 (EP) ..................................... 10005802

(51) Int. Cl.
| | |
|---|---|
| *A01N 43/82* | (2006.01) |
| *A01N 25/02* | (2006.01) |
| *A01N 27/00* | (2006.01) |
| *A01N 37/08* | (2006.01) |
| *A01N 43/54* | (2006.01) |
| *A01N 43/653* | (2006.01) |
| *A01N 43/88* | (2006.01) |

(52) U.S. Cl.
CPC ................ *A01N 27/00* (2013.01); *A01N 25/02* (2013.01); *A01N 37/08* (2013.01); *A01N 43/54* (2013.01); *A01N 43/653* (2013.01); *A01N 43/82* (2013.01); *A01N 43/88* (2013.01)

(58) Field of Classification Search
CPC .............................. A01N 43/82; A01N 25/02
USPC .................................................. 504/261, 139
See application file for complete search history.

(56) References Cited

U.S. PATENT DOCUMENTS

| | | |
|---|---|---|
| 7,098,170 B2 | 8/2006 | Asrar et al. |
| 2007/0149401 A1 | 6/2007 | Haskell et al. |
| 2009/0186762 A1 | 7/2009 | Rademacher et al. |
| 2009/0192040 A1 | 7/2009 | Grobler |
| 2010/0009852 A1 | 1/2010 | Rosinger et al. |
| 2010/0120714 A1* | 5/2010 | Finkelstein et al. ............ 514/63 |
| 2010/0218278 A1 | 8/2010 | Kaster et al. |

OTHER PUBLICATIONS

Vawdrey, L.L. et al., "Field evaluation of strobilurins, triazoles and acibenzolar to control Sigatoka disease in Australia," Infomusa, vol. 14(2), pp. 11-15 (Dec. 2005).*
Madhusudhan, K.N. et al., "Acibenzolar-S-methyl (ASM)-induced resistance against tobamoviruses involves induction of RNA-dependent RNA polymerase (RdRp) and alternative oxidase (AOX) genes," Journal of Crop Science and Biotechnology, vol. 11(2), pp. 127-134 (Jun. 2008).*
CABA abstract 2008:138601 (2008).*
CABA abstract 2010:11132 (2010).*
LaMondia, J.A., "Actigard increases fungicide efficacy against tobacco blue mold," Plant Disease, vol. 92, October issue, pp. 1463-1467 (2008).*
Kawakami et al., J. Plant Growth Regul, 2010, 29: 280-288.

* cited by examiner

*Primary Examiner* — John Pak
(74) *Attorney, Agent, or Firm* — Brian D. McAlhaney

(57) ABSTRACT

The present invention is directed to methods of increasing the environmental stress tolerance of a plant, to methods of improving the quality and/or yield of a plant crop, to methods of application of agrochemicals having a physiological effect on a plant in the plant irrigation water, and to crops produced using said methods.

10 Claims, 1 Drawing Sheet

PLANT IRRIGATION METHODS

This application is a 371 of International Application No. PCT/US2011/039082 filed Jun. 3, 2011, which claims priority to EP 10005802.3 filed Jun. 4, 2010, the contents of which are incorporated herein by reference.

FIELD OF THE INVENTION

The present invention is directed to methods of increasing the environmental stress tolerance of a plant, to methods of improving the quality and/or yield of a plant crop, to methods of application of agrochemicals having a physiological effect on a plant, and to crops produced using said methods.

BACKGROUND

The agrochemical industry is continually seeking methods of improving the growth of plants. Chemicals are typically used to control undesirable species, such as insects or vegetation (e.g. weeds or fungi) and to promote plant growth (e.g., by providing nutrients), thereby improving the growth of plants.

Aside from to direct damage caused by external factors such as plant pests, or the lack of nutrients, the growth of a plant is affected, often detrimentally, by the plant's own responses to external environmental stress factors. When subjected to such stress factors plants display a variety of mechanistic responses as protective measures, with a resultant adverse effect on growth, development, and productivity. Significant losses in quality and yield are commonly observed.

Acibenzolar (benzo[1,2,3]thiadiazole-7-carbothioic S-acid), acibenzolar-S-methyl(S-methyl benzo[1,2,3]thiadiazole-7-carbothioate), and probenazole (3-allyloxy-1,2-benzothiazole 1,1-dioxide), are plant activators that are used for controlling fungi and bacteria. Plant activators are substances that protect plants by activating their defence mechanisms against pests or diseases.

Trinexapac ((RS)-4-cyclopropyl(hydroxy)methylene-3,5-dioxocyclohexanecarboxylic acid), its ethyl ester trinexapac-ethyl, prohexadione (3,5-dioxo-4-propionylcyclohexanecarboxylic acid) and triazoles, such as paclobutrazol ((2RS,3RS)-1-(4-chlorophenyl)-4,4-dimethyl-2-(1H-1,2,4-triazol-1-yl)pentan-3-01), tebuconazole ((RS)-1-p-chlorophenyl-4,4-dimethyl-3-(1H-1,2,4-triazol-1-ylmethyl)pentan-3-ol) and metconazole ((1RS,5RS;1RS,5SR)-5-(4-chlorobenzyl)-2,2-dimethyl-1-(1H-1,2,4-triazol-1-ylmethyl)cyclopentanol) are gibberellic acid synthesis inhibitors. Gibberellic acid is a phytohormone that promotes growth in plants.

Trinexapac-ethyl (TXP) and prohexadione-Ca are used for plant growth regulation in cereals, especially in wheat, and trinexapac-ethyl is also used for the management of growth of warm and cool season turfgrass on golf courses, sod farms, residential lawns and other areas, thereby eliminating the need for frequent mowing and grass clipping. The material is applied by ground sprayers and granule spreaders.

Paclobutrazol (PBZ) is used as a spray on the plant crops of ornamentals and orchards to reduce plant growth and stimulate flowers. It is also used by arborists to reduce shoot growth and has been shown to have additional benefits for trees and shrubs when administered by soil drench or soil injection methods, including improved resistance to drought stress, darker green leaves, protection against some fungal and bacterial pathogens, and enhanced development of fibrous roots. (W. R. Chaney, D. M. Mickey and H. A. Holt; www.pgrsa.org/2005_Proceedings/papers/028.pdf).

Neonicotinoids are used as insecticides applied as a spray and/or seed treatment to protect plant crops from pests. Beside the insecticide effects and beside others, thiamethoxam is used as seed treatment to stimulate the plant growth.

Stobilurins are used as fungicides applied as a spray and/or seed treatment to protect plant crops from disease.

European patent EP 0,220,514 refers to compositions comprising phytohormones and their use in methods for increasing the quantity and quality of fruits or flowers of plants in horticulture or agriculture. International patent application WO 2005/018319 refers to the application of auxins to the roots of plants by drip irrigation or spray application in order to inhibit insect infestation.

There is a need for additional methods for dealing with the environmental stresses experienced by plants in order to increase their tolerance thereto, and to improve the quality and yield of a plant crop subject to those stresses.

SUMMARY OF THE INVENTION

It has surprisingly been found that the application of an agrochemical having a physiological effect on a plant, in the irrigation water, increases the tolerance of the plant to environmental stresses resulting in a plant crop having an improved quality and/or in an increased yield.

Accordingly, in a first aspect, the present invention provides a method of increasing the environmental stress tolerance of a plant comprising the application of one or more agrochemicals in the plant irrigation water wherein said agrochemical has a physiological effect on the plant.

Agrochemicals possessing plant physiological effects, which are considered particularly suitable for use in the methods of the present invention include, for example, plant regulators, plant growth regulators, plant activators, natural and synthetic plant hormones, and plant hormone antagonists. Certain suitable agrochemicals may be known to fulfil one or more of these criteria and plant growth regulators, in particular, may do so.

BRIEF DESCRIPTION OF THE DRAWING

Having thus described the invention in general terms, reference will now be made to the accompanying drawing wherein:

FIG. 1 illustrates soybean plants grown in pouches. On the left-hand side plants treated with ASM and on the right-hand side non treated check plants

DETAILED DESCRIPTION

Particular agrochemicals considered suitable for use in the methods of the present invention include those each independently selected from the group consisting of:

Antiauxins (clofibric acid, 2,3,5-tri-iodobenzoic acid);
Auxins (4-CPA, 2,4-D, 2,4-DB, 2,4-DEP, Dichlorprop, fenoprop, IAA, IBA, Naphthaleneacetamide, α-naphthaleneacetic acid, 1-naphthol, naphthoxyacetic acids, potassium naphthenate, sodium naphthenate, 2,4,5-T);
Cytokinins (2iP, Benzyladenine, kinetin, zeatin);
Defoliants (calcium cyanamide, dimethipin, endothal, ethephon, merphos, metoxuron, pentachlorophenol, thidiazuron, tribufos);
Growth inhibitors (abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, 2,3,5-tri-iodobenzoic acid, morphactins [chlorfluren, chlorflurenol, dichlorflurenol, flurenol], tebuconazole, metconazole);

Growth retardants (chlormequat, daminozide, flurprimidol, mefluidide, paclobutrazol, tetcyclacis, uniconazole);

Growth stimulators (brassinolide, forchlorfenuron, hymexazol, thiametoxam);

Unclassified plant regulators (benzofluor, buminafos, carvone, ciobutide, clofencet, cloxyfonac, cyanamide, cyclanilide, cycloheximide, cyprosulfamide, epocholeone, ethychlozate, fenridazon, heptopargil, holosulf, inabenfide, karetazan, lead arsenate, methasulfocarb, prohexadione, pydanon, sintofen, triapenthenol, trinexapac-ethyl);

Plant activators (acibenzolar, acibenzolar-S-methyl, probenazole);

Salicylates (salicylic acid, sodium salicylate);

Jasmonates (jasmonic acid, methyl jasmonate, cis-jasmone);

Plant peptide hormones (systemin, CLV3/ESR-related ('CLE') peptide family, ENOD40, phytosulfokine, POLARIS, Rapid Alkalinization Factor, SCR/SP11, ROTUNDIFOLIA4/DEVIL1, inflorescence deficient in abscission);

Polyamines;

Strigolactones;

Neonicotinoids;

Triazoles;

Strobilurins; and

Nitric oxide donors.

Particularly suitable agrochemicals include those independently selected from the group consisting of acibenzolar, acibenzolar-S-methyl (ASM), trinexapac-ethyl (TXP), azoxystrobin, propiconazole, thiamethoxam and paclobutrazol (PBZ).

Among the particularly suitable agrochemicals there may be mentioned azoxystrobin, paclobutrazol, trinexapac-ethyl, propiconazole and ASM; and in particular azoxystrobin and ASM.

The agrochemical compounds for use in the methods of the present invention may be in the form of an agrochemically acceptable salt. Agrochemically acceptable salts possess a cation, which is known and accepted in the art for the formation of salts for agricultural or horticultural use. Suitably, the salts are water-soluble. References to agrochemical compounds of the invention herein shall be deemed to also include agrochemically acceptable salts thereof.

The agrochemical compounds for use in the methods of the present invention may be applied as sole ingredients, or alternatively, each agent may be in the form of an agrochemical composition comprising an agrochemically acceptable diluent or carrier. References herein to the agrochemical compounds of the invention or components comprising said compounds shall be deemed to include the compounds as sole ingredients or agrochemical compositions thereof.

A single agrochemical having plant physiological effects may be used in the methods of the present invention. Alternatively, a combination of two or more, such as three or four, such agrochemicals may be used. In the event that two or more agrochemicals having plant physiological effects are used, said agrochemicals may be applied simultaneously or sequentially or a combination thereof. Each agrochemical may be applied directly as separate components or as a mixture of the two. References herein to a combination of agrochemicals having plant physiological effects, and specific embodiments thereof, shall be deemed to include the agrochemicals as separate individual ingredients or as mixtures thereof, or agrochemical compositions of said individual ingredients, or mixtures thereof, comprising an agrochemically acceptable diluent or carrier.

In a further aspect, the present invention provides a method of reducing damage to a plant caused by one or more environmental stress factors, comprising the application of one or more agrochemicals selected from acibenzolar, acibenzolar-S-methyl (ASM), trinexapac-ethyl (TXP), azoxystrobin, propiconazole, thiamethoxam and paclobutrazol (PBZ) in the plant irrigation water wherein said agrochemical has a physiological effect on the plant.

In a further aspect, the present invention provides a method for improving the quality of a plant crop comprising the application of one or more agrochemicals selected from acibenzolar, acibenzolar-S-methyl (ASM), trinexapac-ethyl (TXP), azoxystrobin, propiconazole, thiamethoxam and paclobutrazol (PBZ) in the plant irrigation water wherein said agrochemical has a physiological effect on the plant.

In a further aspect, the present invention provides a method for improving the yield of a plant crop comprising the application of one or more agrochemicals selected from acibenzolar, acibenzolar-S-methyl (ASM), trinexapac-ethyl (TXP), azoxystrobin, propiconazole, thiamethoxam and paclobutrazol (PBZ) in the plant irrigation water wherein said agrochemical has a physiological effect on the plant.

In a further aspect, the present invention provides a method of improving plant vigour comprising the application of one or more agrochemicals selected from acibenzolar, acibenzolar-S-methyl (ASM), trinexapac-ethyl (TXP), azoxystrobin, propiconazole, thiamethoxam and paclobutrazol (PBZ) in the plant irrigation water wherein said agrochemical has a physiological effect on the plant.

In an additional embodiment, the present invention provides a method of increasing the environmental stress tolerance of a plant comprising the application of an agrochemical selected from azoxystrobin, paclobutrazol, trinexapac-ethyl, propiconazole and acibenzolar-S-methyl in the plant irrigation water.

In a further embodiment, the present invention provides a method of reducing damage to a plant caused by one or more environmental stress factors, comprising the application of an agrochemical selected from azoxystrobin, paclobutrazol, trinexapac-ethyl, propiconazole and acibenzolar-S-methyl in the plant irrigation water.

In a further embodiment, the present invention provides a method for improving the quality of a plant crop comprising the application of an agrochemical selected from azoxystrobin, paclobutrazol, trinexapac-ethyl, propiconazole and acibenzolar-S-methyl in the plant irrigation water.

In yet a further embodiment, the present invention provides a method for improving the yield of a plant crop comprising the application of an agrochemical selected from azoxystrobin, paclobutrazol, trinexapac-ethyl, propiconazole and acibenzolar-S-methyl in the plant irrigation water.

In an additional embodiment, the present invention provides a method of improving plant vigour comprising the application of an agrochemical selected from azoxystrobin, paclobutrazol, trinexapac-ethyl, propiconazole and acibenzolar-S-methyl, in the plant irrigation water.

In a further aspect, the present invention provides a crop produced using a method of the present invention.

The methods of the present invention are applicable to any type of environmental stress that a plant may experience during its growth. The methods of the present invention are considered to be particularly suitable wherein the stress experienced by the plant is abiotic stress. In a specific embodiment, the methods of the present invention are applicable when the abiotic stress experienced by a plant during its growth is drought, flood, excessive temperature, low temperature, frost, excess sunlight, insufficient sunlight, wind, inadequate soil nutrients, excessive soil salinity, air pollution, soil pollution or water pollution, or any combination thereof. Most suitably, the stress experienced is drought, excessive temperature or frost, or any combination thereof.

Accordingly, in a more specific embodiment, the present invention provides a method of increasing the environmental stress tolerance of a plant comprising the application of an agrochemical selected from azoxystrobin and acibenzolar-S-methyl in the plant irrigation water, wherein the stress experienced is drought, excessive temperature or frost, or any combination thereof. Most particularly the stress experienced is drought.

In a further more specific embodiment, the present invention provides a method of reducing damage to a plant caused by one or more environmental stress factors, comprising the application of an agrochemical selected from azoxystrobin and acibenzolar-S-methyl in the plant irrigation water, wherein the stress experienced is drought, excessive temperature or frost, or any combination thereof. Most particularly, the stress experienced is drought.

In a further more preferred embodiment, the present invention provides a method for improving the quality of a plant crop comprising the application of an agrochemical selected from azoxystrobin and acibenzolar-S-methyl in the plant irrigation water, wherein the stress experienced is drought, excessive temperature or frost, or any combination thereof. More specifically, the stress experienced is drought.

In a further more preferred embodiment, the present invention provides a method for improving the yield of a plant crop comprising the application of an agrochemical selected from azoxystrobin and acibenzolar-S-methyl in the plant irrigation water, wherein the stress experienced is drought, excessive temperature or frost, or any combination thereof. Most particularly, the stress experienced is drought.

In a further more preferred embodiment, the present invention provides a method of improving plant vigour comprising the application of an agrochemical selected from azoxystrobin and acibenzolar-S-methyl in the plant irrigation water, wherein the stress experienced is drought, excessive temperature or frost, or any combination thereof. Most particularly, the stress experienced is drought.

The term "increasing the yield" of a plant means that the yield of a product of the plant is increased by a measurable amount over the yield of the same product of the plant produced under the same conditions, but without the application of the combinations according to the present invention. It is suitable that the yield is increased by at least about 0.5%, suitably 1%, more suitably 2%, yet more suitably 4% or more. Even more suitably is an increase in yield of at least about 5%, 10%, 15% or 20% or more.

The term "improving plant vigour" means that the vigour rating, or the plant weight, or the plant height, or the plant canopy, or the visual appearance, or any combination of these factors, is increased or improved by a measurable or noticeable amount over the same factor of the plant produced under the same conditions, but without the application of the combinations according to the present invention.

The use of the methods of the invention can be via any suitable irrigation method, which ensures that the one or more agrochemicals penetrate the soil, the rhizosphere or is otherwise absorbed by the plant, for example, localised irrigation, spray irrigation, drip irrigation, bubbler irrigation, sub-soil irrigation, soil injection, seepage irrigation, surface irrigation, flooding, furrow, drench, application through sprinklers, micro-sprinklers or central pivot, or manual irrigation, or any combination thereof.

In a specific embodiment, there may be mentioned sprinkler, subsurface drip and surface drip irrigation.

The rate and frequency of application of the one or more agrochemicals according to the methods of the present invention may vary within wide limits and depends on the type of use, the specific agrochemical, the nature of the soil, the method of application, the plant to be controlled, the prevailing climatic conditions, and other factors governed by the method of application, the time of application and the target plant.

Typical rates of application are normally from 1 g to 2 kg of active ingredient (a.i.) per hectare (ha), suitably from 5 g to 1 kg a.i./ha, more suitably from 20 g to 600 g a.i./ha, yet more suitably from 50 g to 200 g a.i./ha. Most suitably, the rate of application of the compound of formula (I) is 50 g to 200 g/ha, and the rate of application of plant activator is from 5 g to 50 g/ha.

In one embodiment, suitable rates and application timings for the agrochemicals used in the inventive methods are comparable to the existing rates and timings given on the current product labels for products containing such agrochemicals such as azoxystrobin (Quadris®), paclobutrazol (Trimmit®), trinexapac-ethyl(Moddus®), and propiconazole (Tilt®).

Typically, the application of the one or more agrochemicals according to the methods of the present invention can occur on several occasions during the growth of a plant up to the harvest. The one or more agrochemicals may be applied once or on several occasions during the growth of a plant depending on the plant and circumstances, for example, 1 to 6 or 1 to 4 occasions, and the amounts indicated above for each agrochemical are application rates are for each application.

The methods of the present invention may be used for the treatment of any plant including, for example, cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflower, soybean, jatropha, oil palm); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, for example, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutate* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)).

The methods of the present invention are particularly suitable for the treatment of crops, such as field crops, fruits, vegetables, nuts (particularly peanuts), berries, tropical plantations, ornamentals and others, such as wheat, barley, rye, oats, rice, maize, sorghum, beans, lentils, peas, soybeans, rape, mustard, poppy, sugar- and fodder-beet, cotton, flax, hemp, jute, sunflowers, castor oil, groundnuts, potatoes, tobacco, sugar cane, apples, pears, plums, peaches, nectarines, apricots, cherries, oranges, lemons, grapefruit, mandarins, olives vines, hops, almonds, walnuts, hazelnuts, avocado, bananas, tea, coffee, coconut, cocoa, natural rubber plants, oil plants, strawberries, raspberries, blackberries, spinach, lettuce, asparagus, cabbages, Chinese kale, carrots, onions, tomatoes, cucumbers, pepper, eggplants, melons, paprika, chilli, roses, chrysanthemums and carnations. The plants may also be genetically modified.

The present invention may be used in all types of soil, including salty soils, low-high pH soils, sandy-, clay-, loamy, silty soils, low-, high organic matter soils. Suitable plants also include plants that have been rendered tolerant to herbicides like bromoxynil or classes of herbicides (such as HPPD inhibitors, ALS inhibitors; for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones (e.g. imazamox) by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

Suitable plants also include plants which have been so transformed by the use of recombinant DNA techniques that they are capable of synthesising one or more selectively acting toxins, such as are known from toxin-producing bacteria, especially those of the genus *Bacillus*.

Suitable plants also include plants which have been so transformed by the use of recombinant DNA techniques that they are capable of synthesising antipathogenic substances having a selective action, such as the so-called "pathogenesis-related proteins" (PRPs, see e.g. European patent application EP 0,392,225). Examples of such antipathogenic substances and transgenic plants capable of synthesising such antipathogenic substances are known, for example, from European patent applications EP 0,392,225 and EP 0,353,191 and International patent application WO 95/33818. The methods of producing such transgenic plants are generally known to the person skilled in the art and are described, for example, in the publications mentioned above.

The methods of the present invention as defined herein are particularly suitable for the treatment of crops grown for agricultural, ornamental, or forestry purposes, in particular, irrigated or flooded crops. Suitable crops are soybean, maize, rice, cotton, vegetables, banana, jatropha, ornamentals, and wheat; most suitable crops are soybean, maize, vegetables, and wheat.

Accordingly, in a yet more specific embodiment, the present invention provides a method of increasing the environmental stress tolerance of an irrigated crop comprising the application of an agrochemical selected from azoxystrobin and acibenzolar-S-methyl in the plant irrigation water, wherein the stress experienced is drought, excessive temperature or frost, or any combination thereof and the plant is soybean, maize, rice, cotton, vegetables, banana or jatropha. Most suitably the stress experienced is drought and the plant is soybean, maize, rice, cotton, vegetables, banana or jatropha.

In a further more specific embodiment, the present invention provides a method of reducing damage to of an irrigated crop caused by one or more environmental stress factors, comprising the application of an agrochemical selected from azoxystrobin and acibenzolar-S-methyl in the plant irrigation water, wherein the stress experienced is drought, excessive temperature or frost, or any combination thereof. Most suitably the stress experienced is drought and the plant is soybean, maize, rice, cotton, vegetables, banana or jatropha.

In a further more specific embodiment, the present invention provides a method for improving the quality of an irrigated crop comprising the application of an agrochemical selected from azoxystrobin and acibenzolar-S-methyl in the plant irrigation water, wherein the stress experienced is drought, excessive temperature or frost, or any combination thereof. Most suitably the stress experienced is drought and the plant is soybean, maize, rice, cotton, vegetables, banana or jatropha.

In a further more specific embodiment, the present invention provides a method for improving the yield of an irrigated crop comprising the application of an agrochemical selected from azoxystrobin and acibenzolar-S-methyl in the plant irrigation water, wherein the stress experienced is drought, excessive temperature or frost, or any combination thereof. Most suitably the stress experienced is drought and the plant is soybean, maize, rice, cotton, vegetables, banana or jatropha.

In a further more preferred embodiment, the present invention provides a method of improving plant vigour of an irrigated comprising the application of an agrochemical selected from azoxystrobin and acibenzolar-S-methyl in the plant irrigation water, wherein the stress experienced is drought, excessive temperature or frost, or any combination thereof. Most suitably the stress experienced is drought and the plant is soybean, maize, rice, cotton, vegetables, banana or jatropha.

Normally, for control of biotic stress from pests such as insects, weeds and disease, a grower in the management of a crop would use one or more other agronomic chemicals in addition to the agrochemicals of the present invention. Examples of agronomic chemicals for control of biotic stress include pesticides, such as fungicides, herbicides, insecticides, bactericides, acaricides and nematicides, plant nutrients and plant fertilizers.

Accordingly, the present invention provides the methods according to the present invention, which includes the simultaneous and/or sequential application of one or more further agronomic chemicals. Suitably, the one or more further agronomic chemicals are agrochemical compounds and/or plant nutrients and/or plant fertilizers. Suitably, the agrochemical compounds are pesticides, such as fungicides, herbicides, insecticides, bactericides, acaricides and nematicides.

Suitable examples of plant nutrients or plant fertilizers are calcium sulfate $CaSO_4$, calcium nitrate $Ca(NO_3)_2.4H_2O$, calcium carbonate $CaCO_3$, potassium nitrate $KNO_3$, magnesium sulfate $MgSO_4$, potassium hydrogen phosphate $KH_2PO_4$, manganese sulfate $MnSO_4$, copper sulfate $CuSO_4$, zinc sulfate $ZnSO_4$, nickel chloride $NiCl_2$, cobalt sulfate $CoSO_4$, potassium hydroxide KOH, sodium chloride NaCl, boric acid $H_3BO_3$ and metal salts thereof, $Na_2MoO_4$. The nutrients may be present in an amount of 5% to 50% by weight, suitably of 10% to 25% by weight or of 15% to 20% by weight each. Preferred additional nutrients are urea, melamine, potassium oxide, and inorganic nitrates. The most preferred additional plant nutrient is potassium oxide. Where the preferred additional nutrient is urea, it is present in an amount of generally 1% to 20% by weight, suitably 2% to 10% by weight or of 3% to 7% by weight.

Examples of herbicides include glyphosate, glufosinate, glyfosinate, imidazilinones, HPPDs (mesotrione) and STS system (sulfonylurea).

Examples of pesticides include spinosad, avermectin, such as the natural avermectins, A1a, A1b, A2a, A2b, B1a, B1b, B2a and B2b, which can be obtained from *Streptomyces avermitilis*, and avermectin monosaccharide derivatives, such as abamectin, doramectin, emamectin, eprinomectin, ivermectin and selamectin, and milbemycin derivatives, such as milbemectin, milbemycin oxime, moxidectin and S10009.

Examples of nematicides are abamectin, carbamate nematicides (e.g. aldicarb, carbofuran, carbosulfan, oxamyl, aldoxycarb, ethoprop benomyl, alanycarb), organophosphorus nematicides (e.g. phenamiphos, fenamiphos, fensulfothion, terbufos, fosthiazate, phosphocarb, dichlofenthion, isamidofos, fosthietan, isazofos, ethoprophos, cadusafos, chlorpyrifos, heterophos, isamidofos, mecarphon, phorate, thionazin, triazophos, diamidafos, phosphamidon), methyl bromide, methyl iodide, carbon disulfide, 1,3 dichloropropene, chloropicrin, cytokinins, dazomet, DCIP, ethylene dibromide, GY-81, metam, methyl isocyanate, *myrothecium verrucaria* composition, flupyrazofos, benchlothiaz, [2-cyanoimino-3-ethylimidazolidin-1-yl]phosphonothioic acid O-ethyl S-propyl ester, and *bacillus firmus*.

Further suitable examples of pesticides that can be used include acephate, acetamiprid, acetoprole, aldicarb, alpha-cypermethrin, azinphos-methyl, azoxystrobin, benalaxyl, benalaxyl-M, benclothiaz, bendicoarb, benfuracarb, benomyl, bensultap, bifenthrin, bitertanol, boscalid, captan, carbendazim, carbaryl, carbofuran, carbosulfan, carboxin, carbpropamid, chlorothalonil, chlorpyrifos, chlorpyrifos-methyl, clothianidin, copper salts (such as copper sulfate, cuprous oxide, Bordeaux mixture, copper hydroxide, copper sulfate (tribasic), copper oxychloride and copper octanoate), cymoxanil, cypermethrin, cyproconazole, cyprodinil, cyromazine, dazomet, deltamethrin, diazinon, difenoconazole, dimethoate, dimoxystrobin, diniconazole, dinotefuran, Emamectin, endosulfan, ethaboxam, ethirimol, ethiprole, ethoprophos, famoxadone, fenamidone, fenamiphos, fenhexamid, fenpiclonil, fipronil, flonicamid, fluoxastrobin, fluazinam, fludioxonil, fluquinconazole, flutolanil, flutriafol, fonophos, fosetyl-aluminium, fuberidazole, furathiocarb, gamma-cyhalothrin, gamma-HCH, guazatine, heptenophos, hexaconazole, hymexazol, imazalil, imidacloprid, ipconazole, iprodione, isofenphos, lambda-cyhalothrin, mancozeb, maneb, metalaxyl, metalaxyl-M, metconazole, methiocarb, methyl-bromide, methyl-iodide, myclobutanil, nuarimol, omethoate, oxamyl, oxadixyl, oxine-copper, oxolinic acid, pencycuron, pefurazoate, phosmet, picoxystrobin, pirimicarb, prochloraz, procymidone, propamocarb, propiconazole, prothioconazole, pymetrozine, pyraclostrobin, pyrimethanil, pyroquilon, quintozene, silthiofam, spinosad, tebuconazole, tefluthrin, tetraconazole, thiabendazole, thiacloprid, thiamethoxam, thiodicarb, thiophanate-methyl, thiram, tolylfluanid, triadimenol, triazamate, triazophos, triazoxide, triticonazole, trifloxystrobin, 3 Iodo-N*2*-(2-methanesulfonyl-1,1-dimethyl-ethyl)-N*1*-[2-methyl-4-(1,2,2,2-tetrafluoro-1-trifluoromethyl-ethyl)-phenyl]-phthalamide (code NNI-0001), and a compound of 2-Pyridin-2-yl-2H-pyrazole-3-carboxylic acid (2-methylcarbamoyl-phenyl)-amide (code DKI-0001), such as 2-(3-Chloro-pyridin-2-yl)-5-trifluoromethyl-2H-pyrazole-3-carboxylic acid (4-chloro-2-isopropyl-carbamoyl-6-methyl-phenyl)-amide, 2-(3-Chloro-pyridin-2-yl)-5-trifluoromethyl-2H-pyrazole-3-carboxylic acid (4-chloro-2-methyl-6-methylcarbamoyl-phenyl)-amide, 5 bromo-2-(3-chloro-pyridin-2-yl)-2H-pyrazole-3-carboxylic acid (4-chloro-2-isopropyl-carbamoyl-6-methyl-phenyl)-amide, 5-Bromo-2-(3-chloro-pyridin-2-yl)-2H-pyrazole-3-carboxylic acid (4-chloro-2-methyl-6-methylcarbamoyl-phenyl)-amide, and 3-difluoromethyl-1-methyl-1H-pyrazole-4-carboxylic acid (2-bicyclopropyl-2-yl-phenyl) amide.

EXAMPLES

The following examples illustrate further some of the aspects of the invention but are not intended to limit its scope. Where not otherwise specified throughout this specification and claims, percentages are by weight (% w/w).

Examples 1

4 Acibenzolar-S-methyl (ASM)

Soybean plants were grown in pouches (in filter paper bags), and 100 plants each were treated with BION at 3 rates (60, 20, 2 ppm), added to the drench water. Sowing and drench application of BION occurred simultaneously. After 8 days of optimal growth, the pouches went dry and plants were grown for several days under severe drought stress conditions until evaluation (14 days after application). A qualitative assessment was carried out, ranking the plants behaviour into four categories corresponding to four different physiological states (turgescent, slightly withered, strongly withered and desiccated) (Table 1)

TABLE 1

|  |  | Plant Physiological state (number of plants in %) | | | |
| --- | --- | --- | --- | --- | --- |
|  |  | Turgescent | Slightly withered | Strongly withered | Desiccated |
| Treatment | (1) Check untreated | 7.7 | 38.5 | 28.2 | 25.6 |
|  | (2) ASM 60 ppm | 84.8 | 15.2 | 0.0 | 0.0 |
|  | (3) ASM 20 ppm | 84.2 | 7.9 | 2.6 | 5.3 |
|  | (4) ASM 2 ppm | 25.0 | 70.0 | 5.0 | 0.0 |

ASM treated plants behaved much better after severe drought compared to untreated check. While a large majority of the treated plants (more than 80%) were still fully turgescent at the end of the drought period, untreated check plants already dramatically suffered from drought stress.

Examples 5-9

Acibenzolar-S-methyl (ASM) and Thiamethoxam (TMX)

Soybean plants were grown in pouches (in filter paper bags) and either BION or Thiamethoxam was applied to the water at different rates (see FIG. 2). Sowing and drench application of the compounds occurred simultaneously. After 8 days of optimal growth, the pouches went dry and plants were grown under drought stress conditions for 6 days. At the end of the drought period, plants were rewatered and shoot dry weight was determined 2 days later (Table 2). In total, 40 plants per treatment and 40 untreated check plants were assessed.

TABLE 2

| Treatment | | Total Shoot Weight [g] * |
|---|---|---|
| Treatment | (5) Check untreated | 4.3 |
| | (6) ASM 15 ppm | 5.6 |
| | (7) ASM 5 ppm | 4.1 |
| | (8) TMX 12 ppm | 5.8 |
| | (9) TMX 3 ppm | 4.6 |

At higher test rates, both treatments showed a clear increase of shoot dry mass when compared with untreated plants. Additionally, ASM treated plants behaved extremely healthy compared to untreated check, though plants withstand drought much better after ASM treatment (FIG. 1).

Examples 10-13

In this experiment, standardized growth conditions were applied across all corn treatments including: soil-water availability, soil texture and composition, soil chemical and physical properties, meteorological and environmental parameters, and plant nutrition in a greenhouse. No indication of plant disease or pest damage was observed over the course of the study and no pest management program was necessary. A homogeneous sand-organic matter soil mixture (0.18% organic matter) was used as the growth medium in 55-gal containers. These containers were used as a weighing lysimeter, where daily changes in system weight were used to calculate plant transpiration. Four corn plants were grown in each 55-gal container. Three 55-gal containers (12 plants total) made up each treatment. All irrigation and chemical treatments were applied via sub-surface irrigation. Chemical treatments consisted of: azoxystrobin (Quadris), paclobutrazol (Trimmit), trinexapac-ethyl (Moddus), and propiconazole (Tilt) at maximum labeled rates.

Corn plants were grown from seed and transplanted in the 55-gal drums approximately 14 days after planting. Uniform adequate irrigation was applied up to growth stage V3/V4 to ensure plant establishment. Chemical treatment applications were applied at growth stage V3/V4 via sub-surface chemigation. At stage V3/V4, irrigation was decreased to replicate deficit water conditions across all treatments for the remainder of the study period. Irrigation was managed daily to maintain 50% plant-available water. Visual signs of abiotic plant stress were observed approximately 30 days after chemical application. All corn plants were grown to yield and cobs were harvested when kernels were uniformly dry (15% moisture content). Root architecture, specifically relative number of fine roots, was measured at within 2 weeks of harvest using a digital imaging technique. Fine roots are related to water uptake productivity, which is directly tied to the ability of the plant to access soil-water under stress.

Results

Effects of the chemical treatments via sub-surface irrigation on yield and root architecture were specifically documented. The effects are herein reported as the percentage increase compared to the untreated check (12 plants in three containers). As shown in Table 1, all chemigated products under abiotic stress improved yield compared to the untreated check (UTC) by between 3.3 and 16.6% (variability within each treatment was less than 20%). Azoxystrobin, paclobutrazol, and trinexapac-ethyl were statistically different from the control (P values: <0.001 at the $95^{th}$ percentile confidence interval). Similarly, relative number of fine roots for the four treatments were significantly different from the UTC, suggesting that the ability of plants treated with these compounds would be more biologically equipped to access soil-water under abiotic water stress. This is supported by the yield data that showed improved production under abiotic water stress.

TABLE 3

Yield and root architecture results.

| Treatment | Yield (% difference from UTC) | Relative number of fine roots (% difference from UTC) |
|---|---|---|
| Azoxystrobin | 12.5† | 37.3† |
| Paclobutrazol | 16.6† | 70.0† |
| Trinexapac-ethyl | 15.6† | 34.3† |
| Propiconazole | 3.3 | 39.4† |

†indicates statistical significance at the $95^{th}$ percentile confidence interval Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

The invention claimed is:

1. A method of (a) increasing the abiotic environmental stress tolerance of a crop plant under irrigation, (b) improving the quality and/or yield and/or vigour of a crop plant under irrigation, and/or (c) reducing damage to a crop plant caused by one or more abiotic environmental stress factors under irrigation, comprising the application to the crop plant of acibenzolar-S-methyl in the plant irrigation water at a rate from 50 g to 200 g acibenzolar-S-methyl/hectare wherein the concentration of the acibenzolar-S-methyl in the irrigation water is from 2 to 60 ppm.

2. A method according to claim 1 which includes the simultaneous and/or sequential application of one or more further agrochemical compounds and/or plant nutrients and/or plant fertilizers for control of biotic stress from pests.

3. A method according to claim 2 wherein the further agrochemical compound is a pesticide selected from the group consisting of a fungicide, herbicide, insecticide, bactericide, acaricide and nematicide.

4. A method according to claim 1 wherein the plants are crops selected from soybean, maize, rice, cotton, vegetables, banana, jatropha, ornamentals, and wheat.

5. A method according to claim 4 wherein the plants are crops selected from soybean, maize, vegetables and wheat.

6. A method according to claim 1 wherein the abiotic stress is drought, flood, excessive temperature, low temperature, frost, excess sunlight, insufficient sunlight, wind, inadequate soil nutrients, excessive soil salinity, air pollution, soil pollution or water pollution, or any combination thereof.

7. A method according to claim 1 wherein the irrigation is localised irrigation, spray irrigation, drip irrigation, bubbler irrigation, micro-sprinkler irrigation, sub-soil irrigation, seepage irrigation, surface irrigation, flooding, or manual irrigation, or any combination thereof.

8. The method of claim 1, wherein the abiotic environmental stress tolerance of the crop plant is increased.

9. The method of claim 1, wherein the quality and/or yield and/or vigour of the crop plant is improved.

10. The method of claim 1, wherein the damage caused by one or more abiotic environmental stress factors to the crop plant is reduced.

* * * * *